(12) United States Patent
Plata et al.

(10) Patent No.: US 6,197,974 B1
(45) Date of Patent: Mar. 6, 2001

(54) ENANTIOSELECTIVE SYNTHESIS OF 3-AMINOPYRROLIDINES

(75) Inventors: Daniel J. Plata, Wadsworth; Steven A. King, Gurnee, both of IL (US); Frederick A. Plagge, Port Washington, WI (US); Anne E. Bailey, Waukegan; Louis Seif, Buffalo Grove, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/426,237

(22) Filed: Oct. 25, 1999

Related U.S. Application Data

(60) Provisional application No. 60/105,650, filed on Oct. 26, 1998.

(51) Int. Cl.$^7$ .................. C07D 207/14; C07D 209/54
(52) U.S. Cl. ............................. 548/408; 548/557
(58) Field of Search ..................... 548/408, 557

(56) References Cited

U.S. PATENT DOCUMENTS

| | | | |
|---|---|---|---|
| 4,990,517 | 2/1991 | Petersen et al. | 514/300 |
| 5,059,597 | 10/1991 | Petersen et al. | 514/224.5 |
| 5,140,033 | 8/1992 | Schriewer et al. | 514/312 |
| 5,286,723 | 2/1994 | Hayakawa et al. | 514/213 |
| 5,703,244 | 12/1997 | Li et al. | 548/557 |
| 6,013,806 | * 1/2000 | Akiba et al. | 548/408 |
| 6,015,912 | * 1/2000 | Wang et al. | 548/408 |

FOREIGN PATENT DOCUMENTS

| | | |
|---|---|---|
| 9116894 | 11/1991 | (WO). |
| 9415938 | 7/1994 | (WO). |
| 9510519 | 4/1995 | (WO). |

\* cited by examiner

*Primary Examiner*—Joseph McKane
*Assistant Examiner*—Sonya N Wright
(74) *Attorney, Agent, or Firm*—Regina M. Anderson

(57) ABSTRACT

The invention relates to a process of preparing a chiral compound of the formula:

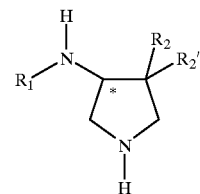

wherein $R_1$ is selected from the group consisting of hydrogen and lower alkyl, and $R_2$ and $R_{2'}$ are the same, and $R_2$ and $R_{2'}$ are selected from a group consisting of hydrogen and primary alkyl, or $R_2$ and $R_{2'}$ taken together form a $C_3$ to $C_6$ cycloalkyl, comprising the steps of chirally reducing a β-keto ester to afford a β-hydroxy ester, activating the β-hydroxy ester by treatment with a sulfonic acid or a derivative thereof to provide an activated compound having sulfonate leaving group, displacing the sulfonate leaving group with an azido moiety, or treating the activated compound with an alkylamine, deprotecting and cyclizing to afford a pyrrolidinone, and reducing the pyrrolidinone to afford a stereoisomerically preferred 3-aminopyrrolidine derivative.

18 Claims, No Drawings

ENANTIOSELECTIVE SYNTHESIS OF 3-AMINOPYRROLIDINES

This application claims the benefit of U.S. Provisional Application Ser. No. 60/105,650, filed Oct. 26, 1998.

TECHNICAL FIELD OF INVENTION

The present invention relates to a process for the preparation of chiral 3-aminopyrrolidine derivatives which have use as intermediates in the preparation of certain pyrido[1,2-a]pyrimidine and quinolone antibacterial agents.

BACKGROUND

The therapeutic use of certain pyrido[1,2-a]pyrimidine derivatives as antibacterial agents has been described in PCT patent applications WO 9116894, published Nov. 14, 1991, and WO 9510519, published Apr. 20, 1995. Quinolone antibacterial agents are well known and are described, for example, in U.S. Pat. Nos. 4,990,517; 5,140,033; 5,059,597; and PCT application WO 9415938. The U.S. Pat. No. 5,286,723 describes amine substituted spiro compounds which are attached to quinoline derivatives for providing compounds having antibacterial use.

Chiral preparation of 3-aminopyrrolidine derivatives via an optically active tartrate ester intermediate is described in U.S. Pat. No. 5,703,244. Enantioselective synthesis of 3-aminopyrrolidine derivatives by chirally reducing a β-hydroxy ester intermediate is not disclosed.

More efficient processes for the preparation of key chiral intermediates for use in the synthesis of antibiotic agents are needed to ensure the ready availability of the compounds. A process of the invention has not previously been described in the prior art.

SUMMARY OF THE INVENTION

A process of the present invention involves efficient enantioselective preparation of chiral 3-aminopyrrolidine and derivatives thereof. The prepared compounds have use as intermediates in the preparation of certain pyrido[1,2-a]pyrimidine and quinolone antibacterial agents.

In one aspect, the invention relates to an enantioselective process for preparing a compound of the formula:

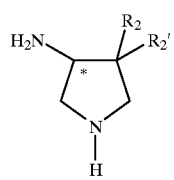

(I)

wherein $R_2$ and $R_{2'}$ are the same, and $R_2$ and $R_{2'}$ are selected from a group consisting of hydrogen and primary alkyl, or $R_2$ and $R_{2'}$ taken together form a $C_3$ to $C_6$ cycloalkyl, comprising the steps of:

(a) chirally reducing a β-keto ester of the formula:

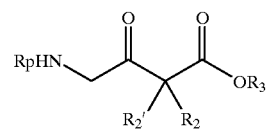

wherein $R_p$ is an amino-protecting group, $R_2$ and $R_{2'}$ are as defined above, and $R_3$ is selected from the group consisting of lower alkyl and aryl, in the presence of an enantiomerically pure ruthenium catalyst to afford a stereoisomerically pure β-hydroxy ester of formula:

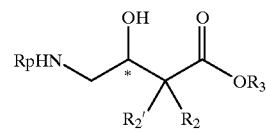

wherein * represents a carbon stereocenter of (R) or (S) configuration;

(b) activating the stereoisomerically pure β-hydroxy ester with sulfonic acid or a derivative thereof to provide an activated β-hydroxy ester of formula:

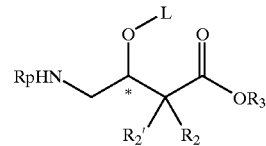

wherein the group represented by the formula —O—L is a sulfonate leaving group;

(c) treating the activated β-hydroxy ester with an azide salt to afford an aminoester azide of the formula:

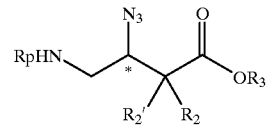

(d) deprotecting and cyclizing the aminoester azide under hydrogenation conditions to afford a pyrrolidinone of the formula:

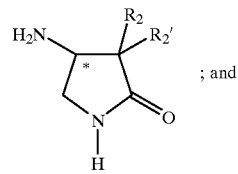

; and (e) reducing the pyrrolidinone.

In another aspect, the invention relates to a process of preparing a sterioisomerically pure compound of formula:

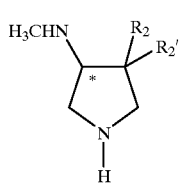

(II)

wherein $R_2$ and $R_{2'}$ are the same, and $R_2$ and $R_{2'}$ are selected from a group consisting of hydrogen and primary alkyl, or $R_2$ and $R_{2'}$ taken together form a $C_3$ to $C_6$ cycloalkyl, comprising the steps of:

(a) protecting the amino moiety of a pyrrolidinone as prepared in step (d) above having a formula:

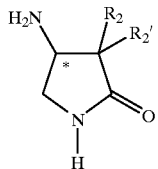

wherein $R_2$ and $R_{2'}$ are as described above, with a compound of formula $R_4COR_5$, wherein $R_4$ is selected from the group consisting of hydrogen, tert-butoxy, fluorenylmethoxy, and benzyloxy, and $R_5$ is hydroxy or a halide selected from the group consisting of bromine, chlorine, fluorine, and iodine, to afford a compound of formula:

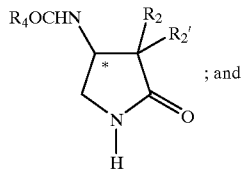

; and (b) reducing the pyrrolidinone.

In yet another aspect, An enantioselective process of preparing a compound of formula:

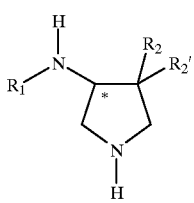

(III)

wherein $R_1$ is selected from the group consisting of hydrogen and lower alkyl, and $R_2$ and $R_{2'}$ are the same, and $R_2$ and $R_{2'}$ are selected from a group consisting of hydrogen and primary alkyl, or $R_2$ and $R_{2'}$ taken together form a $C_3$ to $C_6$ cycloalkyl, comprising the steps of:

(a) chirally reducing a β-keto ester of the formula:

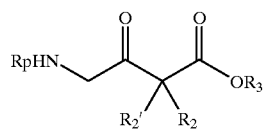

wherein $R_p$ is an amino-protecting group, $R_2$ and $R_{2'}$ are as defined above, and $R_3$ is selected from the group consisting of lower alkyl and aryl, in the presence of an enantiomerically pure ruthenium catalyst to afford a stereoisomerically pure β-hydroxy ester of formula:

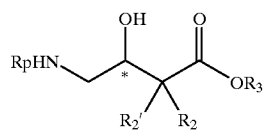

wherein * represents a carbon stereocenter of (R) or (S) configuration;

(b) activating the stereoisomerically pure β-hydroxy ester with sulfonic acid or a derivative thereof to provide an activated β-hydroxy ester of formula:

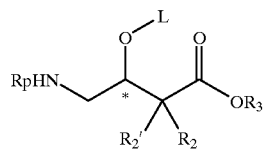

wherein the group represented by the formula —O—L is a sulfonate leaving group;

(c) treating the activated B-hydroxy ester with an amine of the formula $R_1$—$NH_2$, wherein $R_1$ is primary alkyl, to afford a diaminoester of formula:

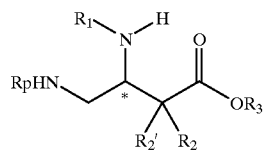

(d) hydrogenating the diaminoester to afford a pyrrolidinone of the formula:

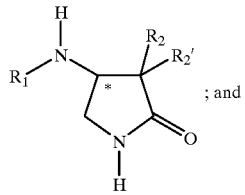

; and (e) reducing the pyrrolidinone.

DETAILED DESCRIPTION OF THE INVENTION

The term "amino-protecting group" as used herein refers to an easily removable group which is known in the art to protect an amino group against undesirable reaction during synthetic procedures and to be selectively removable. The use of amino-protecting groups is well known in the art for protecting groups against undesireable reactions during a synthetic procedure and many such protecting groups are known, cf., for example, T. H. Greene and P. G. M. Wuts, *Protective Groups in Organic Synthesis,* 2nd edition, John Wiley & Sons, New York (1991). Examples of amino-protecting groups include, but are not limited to, acyl groups, including acetyl, trifluoroacetyl, benzoyl, and the like; acyloxy groups, including t-butyloxycarbonyl (BOC), benzyloxycarbonyl (Cbz), fluoroethenylmethoxycarbonyl (Fmoc), and the like.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks of specialized monographs, for example: *Organic Solvents Physical Properties and Methods of Purification,* 4th ed., edited by John A. Riddick, et al., Vol. 11, in the Techniques of Chemistry Series, John Wiley & Sons, NY 1986.

The term "$C_3$–$C_6$-cycloalkyl" as used herein refers to saturated cyclic hydrocarbon radicals containing from three to six carbon atoms. Illustrative of $C_3$–$C_6$-cycloalkyl groups are cyclopropyl, cyclobutyl, cyclopentyl and cyclohexyl.

The term "lower alkyl" as used herein refers to straight or branched chain alkyl radicals containing from 1 to 6 carbon atoms, sometimes represented as Cx-Cy-alkyl where x and y respectively represent the minimum and maximum number of carbon atoms in the alkyl radical. Examples of lower alkyl include, but are not limited to methyl, ethyl, n-propyl, isopropyl, n-butyl, isobutyl, sec-butyl, t-butyl, n-pentyl, 1-methylbutyl, 2,2-dimethylbutyl, 2-methylpentyl, 2,2-dimethylpropyl, n-hexyl, and the like. The term "primary alkyl" as used herein particularly refers to straight chain alkyl radicals of 1 to 6 carbon atoms, for example, methyl, ethyl, n-propyl, n-butyl, n-pentyl, and n-hexyl.

The term "aryl" as used herein refers to an aromatic ring which can be unsubstituted or substituted with one, two, or three substituents including, but not limited to, methyl, alkoxy, amino, and nitro. Illustrative of aryl groups are benzyl, methylbenzyl, dimethylbenzyl, aminobenzyl, nitrobenzyl, benzyloxy, and the like.

The term "primary alkylamine" as used herein refers to an amino group substituted with a primary alkyl group as described above, for example, methylamine, ethylamine, n-propylamine, n-butylamine, n-pentylamine, n-hexylamine, and the like.

Abbreviations which have been used in the descriptions of the schemes and the examples that follow are: BOC for t-butoxycarbonyl; BINAP for 2,2'-bis(diphenylphosphino)-1,1'-binaphthyl; DEAD for diethylazodicarboxylate; DMF for dimethylformamide; $Me_2S$ for dimethyl sulfide; $PPh_3$ for triphenylphosphine; THF for tetrahydrofuran; and Ru-BINAP for diethylammonium-[(bis(2,2'-bis(diphenylphosphino)-1,1'-binaphthyl))-dirutheniumpentachloride];

The process of the invention for preparing 3-aminopyrrolidine derivatives may be applied selectively to prepare specific isomers of 3-aminopyrrolidine compounds. Chiral aminopyrrolidine derivatives may be obtained by reducing a β-keto ester in the presence of an enantiomerically pure ruthenium catalyst to obtain stereoisomerically pure β-hydroxy ester. Chiral integrity is maintained throughout the remaining process, ie. the ratio of (R) to (S) isomers remains nearly in the same proportions, to afford a stereoisomerically pure 3-aminopyrrolidine product.

The process of obtaining specific isomers of the desired 3-aminopyrrolidine compounds may be better understood by reference to Schemes 1, which is illustrated below.

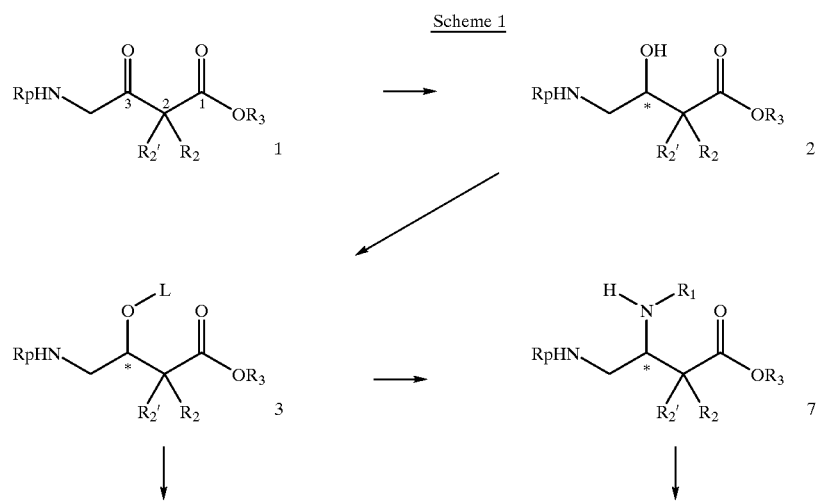

Scheme 1

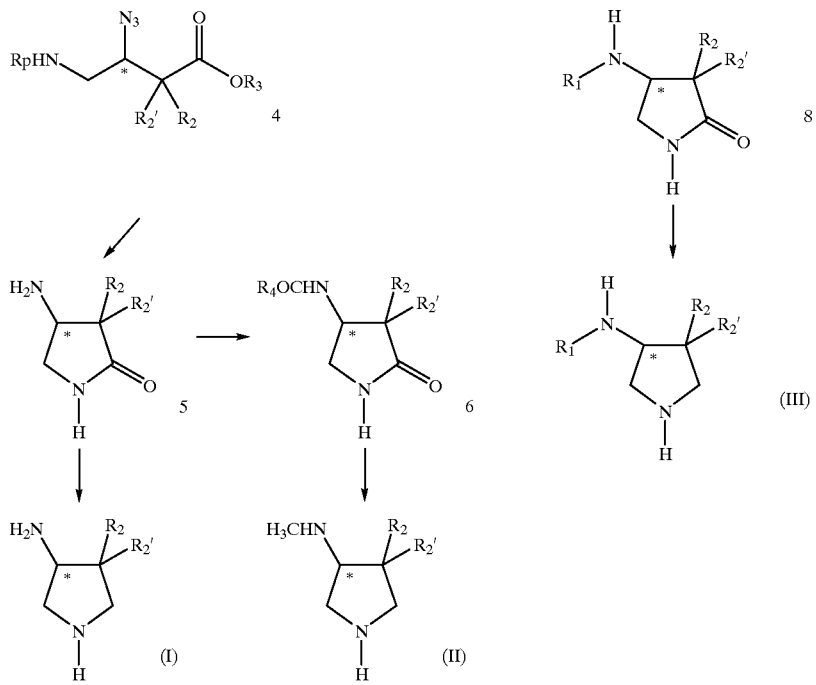

Enantioselective Reduction

Chiral reduction of Compound 1 in the presence of a stereoisomerically pure chiral ruthenium catalyst affords a stereochemically preferred β-hydroxy ester. The reactive Compound 1 comprises a substituted 1,3-β-keto ester. The ester moiety may be represented by the formula —C(O)OR$_3$, wherein R$_3$ represents a lower alkyl or an aryl group and the carbon to which each oxygen atom is attached is the C-1 carbon. The C-2 carbon of the β-keto ester is disubstituted with R$_2$ and R$_2$' to provide an achiral starting compound. Accordingly, R$_2$ and R$_2$' are the same, and R$_2$ and R$_2$' are selected from the group consisting of hydrogen and primary alkyl, or R$_2$ and R$_2$' taken together form a C$_3$ to C$_6$ cycloalkyl moiety. The C-3 carbon of the β-keto ester is substituted with a methylamine group.

A lower alkyl group substitutes the C-1 ester moiety as represented by R$_3$. Suitable lower alkyl groups include, but are not limited to, methyl, ethyl, n-propyl, isopropyl, n-butyl, isobutyl, sec-butyl, t-butyl, n-pentyl, 1-methylbutyl, 2,2-dimethylbutyl, 2-methylpentyl, 2,2-dimethylpropyl, n-hexyl, and the like. Aryl groups suitable for the invention comprise an aromatic ring which can be unsubstituted or substituted with one, two, or three substituents including, but not limited to, methyl, alkoxy, amino, and nitro. Exemplary aryl groups suitable for substituting the ester moiety as represented by R$_3$ include, but are not limited to, benzyl, methylbenzyl, dimethylbenzyl, aminobenzyl, nitrobenzyl, and benzyloxy.

Primary alkyl groups bonded to the C-2 carbon are straight chain alkyl radicals containing from 1 to 6 carbon atoms. Suitable primary alkyl groups include, but are not limited to, methyl, ethyl, n-propyl, n-butyl, n-pentyl, n-hexyl, and the like. Cycloalkyl groups that may substitute the C-2 carbon are cyclopropyl, cyclobutyl, cyclopentyl cyclohexyl, and the like.

The methylamine substituent attached to the C-3 carbon of the β-hydroxy ester is preferably protected with a suitable amino-protecting group as represented by R$_p$. The protected Compound 1 is prepared in accordance with Reference Examples 1 and 2, provided hereinafter in the Examples, or by methods known to those of skill in the art. Suitable amino-protecting groups for the starting compound comprise carbamate protecting groups, as well as aryl-substituted protecting groups. Exemplary carbamate protecting groups comprise the formula —C(O)OR wherein R is hydrogen or alkyl, including, but not limited to, tert-butoxycarbonyl, fluorenylmethoxycarbonyl, and the like. Aryl-substituted protecting groups suitable have a formula —C(O)—Ar, wherein Ar is an aryl or substituted aryl moiety. Typical aryl-substituted protecting groups include, but are not limited to, benzyloxycarbonyl, p-methoxybenzyloxycarbonyl, p-nitrobenzyloxycarbonyl, and the like. Protecting groups and the procedures for synthesizing compounds of protected amino groups are further described in T. H. Greene and P. G. M. Wuts, *Protective Groups in Organic Synthesis*, 2nd edition, John Wiley & Sons, New York (1991), which is herein incorporated by reference.

The preferred starting material comprises a compound as represented by Compound 1, Scheme 1, wherein R$_p$ is an amino-protecting group, R$_2$ and R$_2$' taken together form a C$_3$ to C$_6$ cycloalkyl group, and R$_3$ is lower alkyl. Most preferably, R$_2$ and R$_2$' form a cyclopropyl group, R$_3$ is ethyl, and R$_p$ is selected from the group consisting of tert-butoxycarbonyl, benzyloxycarbonyl, and fluorenylmethoxycarbonyl.

Chiral 3-aminopyrrolidine derivatives may be obtained by chirally reducing the β-keto ester with enantiomerically pure ruthenium catalyst. A preferred ruthenium catalyst of the formula Et$_2$NH$_2$.Ru$_2$Cl$_5$(BINAP)$_2$ exists as two enantiomers, diethylammonium-[(bis((R)-(+)-2,2'-bis(diphenylphosphino)-1,1'-binaphthyl))-dirutheniumpentachloride] and diethylammonium-[(bis((S)-(−)-2,2'-bis(diphenylphosphino)-1,1'-binaphthyl))-dirutheniumpentachloride], respectively referred to hereinafter as (R) Ru-BINAP and (S) Ru-BINAP. Both enantiomers may be prepared from commercially available 2,2'-bis(diphenylphosphino)-1,1'-binaphthyl (BINAP) (Aldrich, U.S.A.) according to methods described by King, et. al., *J. Org. Chem.* 57:6689 (1992).

Specifically when (R) Ru-BINAP is used, (R) 3-aminopyrrolidine derivatives are obtained. Conversely, reduction in the presence of the (S) Ru-BINAP provides (S) 3-aminopyrrolidine derivatives. Preferably, the catalyst is of at least 95% purity, most preferably at least 97% purity. It is believed that other commercially available metal complexing catalysts may also afford the stereochemically preferred product.

The reduction is accomplished in the presence of hydrogen in an inert, alcoholic solvent. The hydrogen source is typically provided in a readily absorbable manner, such as sparging with hydrogen gas. Alcoholic solvents suitable for the reaction include, but are not limited to, methanol, ethanol, isopropanol, and the like, or a mixture thereof. Methanol is the preferred alcoholic solvent.

Heating the reaction mixture before introducing the hydrogen source improves enantiomeric purity of the resulting compound. Temperatures of at least 60° C. may provide a sufficient amount of additional heat, however, it is most preferred that the reaction is heated to at least 100° C. In addition, the reaction is sparged with an inert gas while heating. Suitable inert gases include, but are not limited to, argon, nitrogen, and the like. The most preferred inert gas is nitrogen.

Activation

Activation of Compound 2 involves treating the compound with a derivative of sulfonic acid to prepare a leaving group from the hydroxy moiety.

Suitable reagents for the activation reaction comprise benzenesulfonic acids, p-toluenesulfonic acids, methanesulfonic acids, and the like. Derivatives of the named reagents are also suitable for the reaction, such as acyl halides and acid anhydrides. The preferred group of reagents are methanesulfonic acids. Acyl halide derivatives of methanesulfonic acids are the more preferred class of reagents. Most preferably, the reagent is methanesulfonyl chloride.

Nonpolar aprotic solvents provide a suitable medium for the reaction. Solvents suitable for the reaction include, but are not limited to, isopropyl acetate, diethyl ether, benzene, toluene, pentane, hexane, methylene chloride, chloroform, tetrahydrofuran, methyl-t-butyl ether, and the like, or a mixture thereof. Preferably, the solvent is isopropyl acetate.

The reaction is typically carried out in the presence of weak base. Preferably, the weak base is selected from the group consisting of amines or cyclic amines. Exemplary suitable weak bases include, but are not limited to, triethylamine, piperidine, pyridine, N-methylpiperidine, N-methylmorpholine, N,N-diisopropylamine, and the like. The most preferred weak base is triethylamine.

Preparation of the Azide

Treating Compound 3 with an azide salt displaces the activated leaving group of the β-hydroxy ester with an azido moiety in a reaction that inverts the stereochemistry at the C-3 stereocenter of the β-keto ester moiety. The azide salt is reacted with the activated Compound 3 in a polar, aprotic medium. Suitable azide salts are selected from the group consisting of lithium azide, sodium azide, and potassium azide. The preferred salt is sodium azide. Preferred polar aprotic solvents are selected from the group consisting of acetone, acetonitrile, dimethylformamide, dimethyl sulfoxide, N-methylpyrrolidine, and the like. Preferably, the solvent is dimethylformamide.

The reaction mixture is purged with an inert gas. The preferred inert gas is nitrogen. Typically, the reaction is accomplished from about 40° C. to about 90° C. Preferably, the temperature of the reaction mixture is maintained between 50° C. and 80° C.

Hydrogenation

Hydrogenation deprotects and spontaneously cyclizes Compound 4 to afford a pyrrolidinone as represented by Compound 5 of Scheme 1. The hydrogenation is accomplished in the presence of a metal catalyst in an alcoholic solvent. Purging the reaction mixture with hydrogen gas provides a suitable hydrogen source for the hydrogenation. Typical catalysts for the reaction are palladium or platinum catalysts. Suitable palladium catalysts are selected from the group consisting of palladium on charcoal, palladium black, and the like. Platinum catalysts, for example, platinum black, may also be used. The preferred catalyst is palladium on charcoal. Most preferably, the catalyst is 10% palladium on charcoal.

Exemplary suitable alcoholic solvents include, but are not limited to, methanol, ethanol, isopropanol, and the like, or a mixture thereof. The most preferred alcoholic solvent is methanol.

Reduction

The pyrrolidinone, Compound 5, is reduced with a reducing agent to afford the preferred enantiomer of 3-aminopyrrolidine of formula (I). Reducing reagents suitable for the reaction are generally selected from metal hydrides and borane reagents. Exemplary metal hydrides are include, but are not limited to, lithium aluminum hydride, lithium tri-(-butoxyaluminohydride, aluminum hydride, and the like. Lithium aluminum hydride is preferred metal hydride. Borane reducing reagents suitable for the reaction include, but are not limited to, borane and borane complexes, such as $BH_3.THF$ and $BH_3.Me_2S$. Suitable solvents are nonpolar, aprotic solvents including, but not limited to, diethyl ether, benzene, toluene, pentane, hexane, methylene chloride, chloroform, tetrahydrofuran, methyl-t-butyl ether, and the like, or a mixture thereof. Acidic workup of the reduction reaction results in an acid addition salt of a compound of formula (1).

Amine Derivatization

Compound 5 of Scheme 1 may be optionally derivatized as a suitable carbamate (Compound 6). Derivatization is followed by reduction to achieve methylation as represented by Compound (11). Compounds suitable for the derivatization of the amino group may be represented by the formula $R_4C(O)R_5$, wherein $R_4$ is selected from the group consisting of hydrogen, tert-butoxy, benzyloxy, and fluorenylmethoxy, and $R_5$ is hydroxy or a halide selected from the group consisting of bromine, chlorine, fluorine, and iodine. Preferably, $R_4$ is hydrogen or tert-butyoxy, wherein the amino moiety is protected as its N-formyl amide or N-BOC carbamate. The reduction is accomplished by treating the protected amino moiety with metal hydrides and borane reagents in the preparation of Compound (I).

Direct Amination

Another suitable method of obtaining the pyrrolidinone from the activated 6-hydroxy ester involves directly aminating Compound 3 of Scheme 1 by reaction with an alkylamine. Preferably, the reagent is a primary alkylamine. Exemplary alkylamines include, but are not limited to, methylamine, ethylamine, n-propylamine, n-butylamine, n-pentylamine, n-hexylamine, and the like. The preferred reagent is methylamine. The reaction is carried out with purging under an inert gas. Nitrogen is the most preferred inert gas. The aminated product may be deprotected and cyclized (Compound 7), and then reduced (Compound 8) to afford a chiral 3-aminopyrrolidine of formula (III).

Preparation of a Salt

The compound of formula (I), (II), or (III) can be used as free compounds or as acid addition salts thereof. Suitable acid addition salts comprise inorganic salts as well as organic salts. Exemplary inorganic salts include, but are not limited to, hydrobromide, hydrochloride, hydroiodide, nitrate, phosphate, and sulfate. Suitable organic salts include, but are not limited to, acetate, citrate, fumarate, lactate, maleate, methanesulfonate, benzenesulfonate, and toluenesulfonate.

Preparation of these salts can be accomplished by methods known to those of skill in the art. The salts can be prepared in situ during the final isolation and purification of the 3-aminopyrrolidine, or separately by reacting the free base function with a suitable acid. Methods of preparing acid addition salts are summarized in S. M. Berge, el al, *J. Pharmaceutical Sciences, 66:1–19* (1977), which is herein incorporated by reference.

It is understood that the foregoing detailed description and accompanying examples are merely illustrative and are not to be taken as limitations upon the scope of the invention, which is defined solely by the appended claims and their equivalents. Various changes and modification to the disclosed embodiments will be apparent to those skilled in the art. Such changes and modification, including without limitation those relating to the chemical structures, stereochemistry, substituents, derivatives, intermediates, syntheses, formulations and/or methods of use of the invention, may be made without departing from the spirit and scope thereof.

EXAMPLES

Preparation of reagents, compounds, and materials utilized in the synthesis of compounds f the invention are described herein in the following Reference Examples.

Reference Example 1

Ethyl 4-(N-Cbz)amino-3-oxo-butyrate

The title compound was prepared in accordance with the methods described in Moyer, M. P., Feldman P. L., Rapoport, H., *J. Org. Chem.* 50(25), 5223–5230 (1985). Cbz-glycine was coupled with the magnesium salt of hydrogen ethyl malonate via its imidazolide active ester to afford ethyl 4-(N-Cbz)amino-3-oxo-butyrate.

Reference Example 2

Ethyl 4-(N-Cbz)amino-3-oxo-2-(spirocyclopropyl) butyrate

To 1-(N-Cbz)amino-2-oxo-butyrate (150 g, 538 mmol), was added dibromoethane (69 mL, 800 mmol), potassium carbonate (300 g, 2170 mmol), and DMSO (750 mL) at room temperature. The mixture was stirred overnight. The reaction was monitored by HPLC on a Zorbax SB-Phenyl™ column at 35° C. by gradient elution from 40:60 acetonitrile/water to 80:20 acetonitrile/water (0.1% $H_3PO_4$). Retention time for the desired product was 10.1 minutes at a flow rate of 1.5 mL/min. The product mixture was poured into 1 L of toluene and filtered. The filtrate was diluted with 2 L of deionized water and 200 mL of saturated sodium chloride solution. The organic layer was separated from the filtrate and washed with a mixture of water and saturated sodium chloride solution. The organic layer was filtered through silica gel (75 g) and the pad was washed with an additional 1 L of toluene. The filtrate was concentrated to approximately 150 g. The yellow concentrate was assayed by HPLC at 96 g (60% yield). $^1$H NMR (300 MHz, $CDCl_3$): δ 7.35 (bs, 5H), 5.48(bs, 1H), 5.1 1(s, 2H), 4.59(d, 2H, J=5.1 Hz), 4.21(q, 2H, J=7.0 Hz), 1.58(bs, 4H), 1.29(t, 3H, J=7.0 Hz).

Preparation of the specific isomers of the desired 3-aminopyrrolidine compounds as illustrated in Scheme 1 may be better understood by reference to the Examples below.

Example 1

4-(N-Cbz)amino-3-hydroxy-2-(spirocyclopropyl) butyrate

To a solution of 4-(N-Cbz)amino-3-oxo-2-(spirocyclopropyl)butyrate (58.3 g, 191 mmol) in toluene was added 2 N HCl in EtOH (1.5 mL). The mixture was diluted with ethanol (300 mL) in a pressure vessel. (R) Ru-BINAP catalyst (452 mg, 0.27 mmol) was added. The resulting solution was sparged under one atmosphere of nitrogen and heated to 100° C. The mixture was exposed to hydrogen for two hours and cooled to room temperature. The ethanol was distilled off and ethyl acetate (100 mL) was added. The solution was concentrated to a total volume of 150 mL. Hexanes (900 mL) were slowly added with vigorous stirring and the mixture was stirred at room temperature for an additional 1 hr. Filtration of the resulting solution afforded the desired product (47 g, 82% yield). The product contained less than 2% of the undesired enantiomer as shown by HPLC analysis. HPLC conditions: Chiralcel OD; flow 1.0 mL/min; 90:10 hexane/ethanol; UV detection at 210 nm. Retention times: desired enantiomer—9.10 min.; undesired enantiomer 11.31 min. M.P.: 88–89 ° C.; M/S $[M+H]^+$: 308; M/S $[M+NH_4]^+$: 325; $^1$HNMR ($CDCl_3$): 7.35 (m, 5H), 5.32 (broad, 1H), 5.09 (s, 2H), 4.12 (q, J=6.9 Hz, 2H), 3.59–3.31 (m, 3H), 1.30–1.21 (m, 5H), 0.944 (m, 2H); $^{13}$CNMR ($CDCl_3$): 174.2 (q), 156.9 (q), 136.4 (q), 128.5 (CH), 128.1 (CH), 128.0 (CH), 74.3 (CH), 66.8 ($CH_2$), 60.8 ($CH_2$), 45.3 ($CH_2$), 25.9 (q), 14.6 ($CH_2$), 14.1 ($CH_3$), 12.5 ($CH_2$).

Example 2

(R) Ethyl 4-(N-Cbz)amino-3-methanesulfonyloxy-2-(spirocyclopropyl) butyrate

The 4-(N-Cbz)amino-3-hydroxy-2-(spirocyclopropyl) butyrate (80.8 g, 0.263 mol) was charged into a 2 L, 3-necked round-bottom flask equipped with a mechanical stirrer, thermocouple and addition funnel. Isopropyl acetate (550 mL) was added followed by addition of triethylamine (55 mL, 0.390 mol). The mixture was stirred and cooled to an internal temperature of +2 C. Methanesulfonyl chloride (25 mL, 0.32 mol) was added via the addition funnel portionwise over a period of 10 minutes, while maintaining the internal temperature below +12 C. The reaction mixture was removed from cooling conditions and allowed to warm to ambient temperature for 30 minutes. The reaction was monitored by HPLC on a Zorbax SB-C8™ column (25 cm x 4.6 mm) at ambient temperatures by gradient elution from 30:70 acetonitrile/water to 70:30 acetonitrile/water (0.1% phosphoric acid). The mesylate compound eluted at 10.7 minutes at a flow rate of 1.5 mL/min.

Water (500 mL) was introduced into the mesylate mixture and stirred for 5 minutes. The layers were separated and the aqueous layer extracted with 200 mL IPAc. The organic layers were combined and washed with water (500 mL) and saturated sodium chloride solution (500 mL). The organic layer was concentrated to afford a 90–95 wt % solution in IPAc. The estimated yield (95%) was determined by $^1$H NMR. M/S [M+NH$_4$]$^+$: 403; M/S [M—OMs]$^+$: 290; $^1$HNMR (CDCl$_3$): 7.34 (m, 5H), 5.4 (broad, 1H), 5.1 (d J=5.8 Hz, 2H), 4.56 (dd J=4.4 Hz, 4 Hz, 1H), 4.15 (q J=10 Hz, 2H), 3.72 (m, 2H), 2.98 (s, 3H), 1.46–1.16 (m, 7H).

EXAMPLE 3

(S) Ethyl 4-(N-Cbz)amino-3-azido-2-(spirocyclopropyl)butyrate

The (R) Ethyl 4-(N-Cbz)amino-3-methanesulfonyloxy-2-(spirocyclopropyl) butyrate (84.9 g, 0.22 mol) was dissolved in DMF (440 mL) and charged into a 1 L, 1-necked round bottom flask, equipped with a N$_2$ inlet. Sodium azide (25.1 g, 0.386 mol) was added in one portion and the heterogeneous mixture heated to 80° C. for 45 minutes. The reaction was monitored by HPLC on a Zorbax SB-CTM column (25 cm×4.6 mm). The azide compound eluted at 12.5 minutes at a flow rate of 1.5 mL/min.

The reaction mixture was treated with 1.5 L water and extracted with 1 L toluene. The organic layer was washed with NaCl solution (600 mL) and the organic layer filtered through silica gel (76 g). The silica gel pad was washed with toluene (300 mL) and the organic solution was concentrated. Heptane (200 mL) was added to the flask and the remaining solution was concentrated to afford a 65–70 wt % solution in heptane. Heptane was used to displace residual toluene. The yield (80.6%) of the desired product was determined by HPLC against a known standard. M/S [M+H]$^+$: 333 [M+NH$_4$]$^+$: 350; $^1$HNMR (CDCl$_3$): 7.35 (m, 5H), 5.21 (broad, 1H), 5.1 (d J=4.5Hz, 2H), 4.15 (q J=7.5 Hz, 2H), 3.66–3.36 (m, 3H), 1.4–1.31 (m, 2H), 1.25 (t J=7.5 Hz, 3H), 1.01–0.91 (m, 2H); $^{13}$CNMR (CDCl$_3$): 172.32 (q), 156.28 (q), 136.25 (q), 128.49 (CH), 128.15 (CH), 128.04 (CH), 66.86 (CH$_2$), 64.47 (CH), 61.05 (CH$_2$), 43.39 (CH$_2$), 24.97 (q), 14.06 (CH$_3$), 13.78 (CH$_2$), 13.57 (CH$_2$).

Example 4

(R) 7-amino-5-azaspiro[2,4]heptane-4-one

A 2-liter Parr bottle charged with 10% Pd/C (14.73 g) was sparged with nitrogen gas. Anhydrous EtOH (50 mL) was added to wet the catalyst. The azide was dissolved in EtOH (700 mL) and added to the reaction mixture. The Parr bottle was placed on a shaker, vented 3 times with 4 atm of hydrogen, and then shaken for 2 hours at ambient temperatures under 4 atm of hydrogen. The reaction exothermed to 37° C. The reaction vessel was sparged with hydrogen (2×) and heated to 80° C. for 18 hours under 4 atm of hydrogen. The solution was cooled to room temperature and filtered through a 20 micron Millipore filter. Concentration of the filtrate afforded the desired product. The reaction was monitored by TLC (50:35:10:5 of chloroform/methanol/water/acetic acid) and afforded a light-colored solid (90% yield). Purity of the obtained product was assayed by HPLC against a known standard (80% purity). The aminopyrrolidinone was derivatized to (R) 7-(N-BOC)amino-5-azaspiro[2,4] heptane-4-one and analyzed for chiral purity by chiral HPLC The product contained less than 1% of the undesired enantiomer as shown by HPLC analysis. HPLC conditions: ChiralPak AS™ column (4.6 x 250 mm); flow 1.0 mL/min.; 85:15 hexane/ethanol; UV detection at 210 nm. $^1$H NMR (300 MHz, CDCl$_3$): δ 6.26 (bs, 1H), 3.77 (ddd, 1H, J=16.9, 2.4, 1.1, 0.7 Hz), 3.50 (dd, 1H, J=7.0, 4.4 Hz), 3.12 (ddd, 1H, J=9.6, 4.8, 0.7 Hz), 1.20 (m, 1H), 0.99 (m, 2H), 0.78 (m, 1H).

Example 5

(R) 7-amino-5-azaspiro[2,4]heptane dihydrochloride

Lithium aluminum hydride (LiAlH$_4$) (6.0 g, 158.7 mmol) was charged to a 500 mL 1-necked round-bottomed flask. THF (150 mL) was added. The resulting slurry was stirred and (R) 7-amino-5-azaspiro[2,4]heptane-4-one was added in portions. The flask was fitted with a reflux condenser and a nitrogen inlet. The reaction mixture was heated to reflux overnight, then cooled to ambient temperature. Completion of the reaction was monitored by TLC in an eluting solvent system of 50:35:5:10 of chloroform/methanol/acetic acid/water. Water (6 mL) was added dropwise and stirred for 15 minutes. NaOH (6 mL) was added and the mixture stirred 15 minutes. Water (18 mL) was added and the white suspension was stirred 30 minutes, then filtered through a pad of celite. The celite pad was rinsed with hot THF, and the combined organics were concentrated to an oil. The resulting oil was refluxed with 1 M HCl in MeOH for 2 hours, then cooled and concentrated to a foam. The foam was dissolved into solution in a minimal amount of hot MeOH. Ethyl acetate was added to the resulting solution until the mixture developed a cloudy appearance. Recrystallization afforded a precipitate, which was collected after 4 hours and purified to afford the desired product (4.1 g, 56% yield). $^1$H NMR (300 MHz, CD$_3$OD): δ 3.94 (dd, 1H, J=13.6, 6.2 Hz), 3.51–3.70 (m, 3H), 3.10 (d, 1H, J=12.1 Hz), 1.22–0.86 (m, 4H)

What is claimed is:

1. An enantioselective process for preparing a compound of the formula:

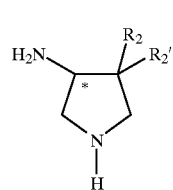

(I)

wherein R$_2$ and R$_2'$ are the same, and R$_2$ and R$_2'$ are selected from a group consisting of hydrogen and primary alkyl, or R$_2$ and R$_2'$ taken together form a C$_3$ to C$_6$ cycloalkyl, comprising the steps of:

(a) chirally reducing a β-keto ester of the formula:

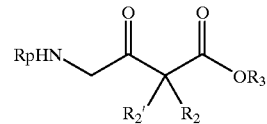

wherein R$_p$ is an amino-protecting group, R$_2$ and R$_2'$ are as defined above, and R$_3$ is selected from the group consisting of lower alkyl and aryl, in the presence of an enantiomerically pure ruthenium catalyst to afford a stereoisomerically pure β-hydroxy ester of formula:

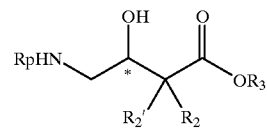

wherein * represents a carbon stereocenter of (R) or (S) configuration;

(b) activating the stereoisomerically pure β-hydroxy ester with sulfonic acid or a salt thereof to provide an activated B-hydroxy ester of formula:

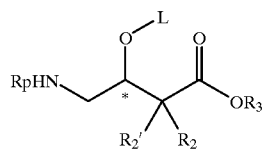

wherein the group represented by the formula —O—L is a sulfonate leaving group;

(c) treating the activated β-hydroxy ester with an azide salt to afford an aminoester azide of the formula:

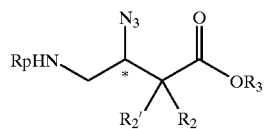

(d) deprotecting and cyclizing the aminoester azide under hydrogenation conditions to afford a pyrrolidinone of the formula:

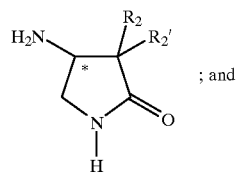

; and (e) reducing the pyrrolidinone to the desired product of formula II.

2. A process according to claim 1, further comprising preparing a hydrochloride salt from the compound in claim 1.

3. A process of preparing a sterioisomerically pure compound of formula:

(II)

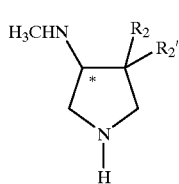

wherein $R_2$ and $R_{2'}$ are the same, and $R_2$ and $R_{2'}$ are selected from a group consisting of hydrogen and primary alkyl, or $R_2$ and $R_{2'}$ taken together form a $C_3$ to $C_6$ cycloalkyl, comprising the steps of:

(a) protecting the amino moiety of a pyrrolidinone as prepared in step (d) of claim 1 having a formula:

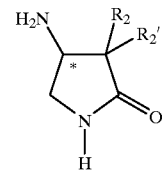

wherein $R_2$ and $R_2$ are as described above, with a compound of formula $R_4COR_5$, wherein $R_4$ is selected from the group consisting of hydrogen, tert-butoxy, fluorenylmethoxy, and benzyloxy, and $R_5$ is hydroxy or a halide selected from the group consisting of bromine, chlorine, fluorine, and iodine, to afford a compound of formula:

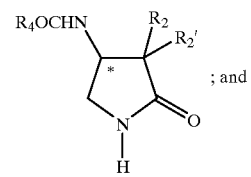

; and (b) reducing the pyrrolidinone to the desired product of formula II.

4. A process according to claim 3, further comprising preparing a hydrochloride salt from the compound in claim 3.

5. An enantioselective process of preparing a compound of formula:

(III)

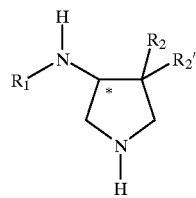

wherein $R_1$ is selected from the group consisting of hydrogen and lower alkyl, and $R_2$ and $R_{2'}$ are the same, and $R_2$ and $R_{2'}$ are selected from a group consisting of hydrogen and primary alkyl, or $R_2$ and $R_{2'}$ taken together form a $C_3$ to $C_6$ cycloalkyl, comprising the steps of:

(a) chirally reducing a β-keto ester of the formula:

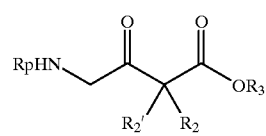

wherein $R_p$ is an amino-protecting group, $R_2$ and $R_{2'}$ are as defined above, and $R_3$ is selected from the group consisting of lower alkyl and aryl, in the presence of an enantiomerically pure ruthenium catalyst to afford a stereoisomerically pure β-hydroxy ester of formula:

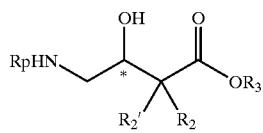

wherein * represents a carbon stereocenter of (R) or (S) configuration;

(b) activating the stereoisomerically pure β-hydroxy ester with sulfonic acid or a salt thereof to provide an activated β-hydroxy ester of formula:

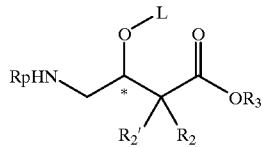

wherein the group represented by the formula —O—L is a sulfonate leaving group;

(c) treating the activated 13-hydroxy ester with an amine of the formula $R_1$—$NH_2$, wherein $R_1$ is primary alkyl, to afford a diaminoester of formula:

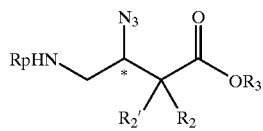

(d) hydrogenating the diaminoester to afford a pyrrolidinone of the formula:

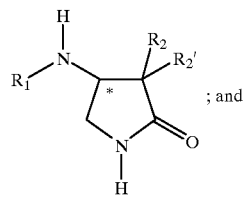

; and (e) reducing the pyrrolidinone to the desired product of formula III.

6. A process according to claim 5, further comprising preparing a hydrochloride salt from the compound in claim 5.

7. A process according to claim 1, wherein the amino-protecting group of the β-keto ester in step (a) is selected from the group consisting of tert-butoxycarbonyl, fluorenylmethoxycarbonyl, benzyloxycarbonyl, p-methoxybenzyloxycarbonyl, and p-nitrobenzyloxycarbonyl.

8. A process according to claim 5, wherein the amino-protecting group of the β-keto ester in step (a) is selected from the group consisting of tert-butoxycarbonyl, fluorenylmethoxycarbonyl, benzyloxycarbonyl, p-methoxybenzyloxycarbonyl, and p-nitrobenzyloxycarbonyl.

9. A process according to claim 1, wherein $R_2$ and $R_{2'}$ are selected from the group consisting of methyl, ethyl, n-propyl, n-butyl, n-pentyl, and n-hexyl.

10. A process according to claim 3, wherein $R_2$ and $R_{2'}$ are selected from the group consisting of methyl, ethyl, n-propyl, n-butyl, n-pentyl, and n-hexyl.

11. A process according to claim 5, wherein $R_2$ and $R_{2'}$ are selected from the group consisting of methyl, ethyl, n-propyl, n-butyl, n-pentyl, and n-hexyl.

12. A process according to claim 1, wherein $R_2$ and $R_{2'}$ taken together form cyclopropyl.

13. A process according to claim 3, wherein $R_2$ and $R_{2'}$ taken together form cyclopropyl.

14. A process according to claim 5, wherein $R_2$ and $R_{2'}$ taken together form cyclopropyl.

15. A process according to claim 1, wherein the catalyst in step (a) is selected from the group consisting of diethylammonium-[(bis((R)-(+)-2,2'-bis(diphenylphosphino)-1,1'-binaphthyl))-dirutheniumpentachloride] and diethylammonium-[(bis((S)-(−)-2,2'-bis(diphenylphosphino)-1,1'-binaphthyl))-dirutheniumpentachloride].

16. A process according to claim 3, wherein the catalyst in step (a) is selected from the group consisting of diethylammonium-[(bis((R)-(+)-2,2'-bis(diphenylphosphino)-1,1'-binaphthyl))-dirutheniumpentachloride] and diethylammonium-[(bis((S)-(−)-2,2'-bis(diphenylphosphino)-1,1'-binaphthyl))-dirutheniumpentachloride].

17. A process according to claim 1, wherein the sulfonate leaving group in step (b) is selected from the group consisting of benzenesulfonate, methanesulfonate, and p-toluenesulfonate.

18. A process according to claim 5, wherein the sulfonate leaving group in step (b) is selected from the group consisting of benzenesulfonate, methanesulfonate, and p-toluenesulfonate.

* * * * *

UNITED STATES PATENT AND TRADEMARK OFFICE
CERTIFICATE OF CORRECTION

PATENT NO. : 6,197,974 B1  Page 1 of 1
DATED : March 6, 2001
INVENTOR(S) : Daniel J. Plata et al.

It is certified that error appears in the above-identified patent and that said Letters Patent is hereby corrected as shown below:

Column 15,
Line 41, replace "product of formula II." with -- product of formula I. --.

Column 17,
Line 24, replace "treating the activated 13-hydroxy ester" with -- treating the activated B-hydroxy ester --.
Line 27, replace " 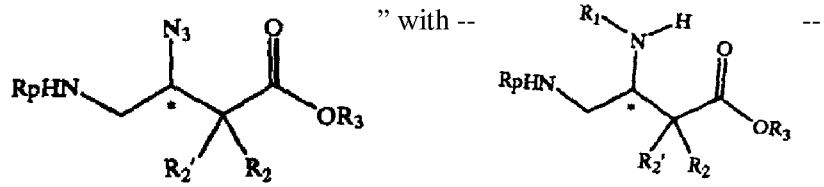 " with -- --

Signed and Sealed this

Eighteenth Day of June, 2002

Attest:

Attesting Officer

JAMES E. ROGAN
Director of the United States Patent and Trademark Office